United States Patent
Exposito Ollero et al.

(10) Patent No.: US 10,568,670 B2
(45) Date of Patent: Feb. 25, 2020

(54) INTRAMEDULLARY FIXATION DEVICE (71) Applicants: UNIVERSITAT POLITECNICA DE VALENCIA, Valencia (ES); UNIVERSITAT DE VALENCIA, Valencia (ES); FUNDACION PARA LA INVESTIGACION DEL HOSPITAL CLINICO DE LA COMUNIDAD VALENCIANA (INCLIVA), Valencia (ES)

(72) Inventors: Jose Exposito Ollero, Valencia (ES); Jose Albelda Vitoria, Valencia (ES); Juan Victor Hoyos Fuentes, Valencia (ES); Ana Valles Lluch, Valencia (ES); Antonio Silvestre Munoz, Valencia (ES)

(73) Assignees: UNIVERSITAT POLITECNICA DE VALENCIA, Valencia (ES); UNIVERSITAT DE VALENCIA, Valencia (ES); FOUNDACION PARA LA INVESTIGACION DEL HOSPITAL CLINICO DE LA COMUNIDAD VALENCIANA (INCLIVA), Valencia (ES)

( * ) Notice: Subject to any disclaimer, the term of this patent is extended or adjusted under 35 U.S.C. 154(b) by 0 days.

(21) Appl. No.: 16/311,478

(22) PCT Filed: Sep. 18, 2017

(86) PCT No.: PCT/ES2017/070619
§ 371 (c)(1),
(2) Date: Dec. 19, 2018

(87) PCT Pub. No.: WO2018/050944
PCT Pub. Date: Mar. 22, 2018

(65) Prior Publication Data
US 2019/0380751 A1 Dec. 19, 2019

(30) Foreign Application Priority Data

Sep. 19, 2016 (ES) .................................. 201631220

(51) Int. Cl.
*A61B 17/72* (2006.01)
*A61F 2/36* (2006.01)
(Continued)

(52) U.S. Cl.
CPC ...... *A61B 17/7275* (2013.01); *A61F 2/30749* (2013.01); *A61F 2/3601* (2013.01);
(Continued)

(58) Field of Classification Search
CPC ............ A61B 17/7216; A61B 17/7275; A61B 17/7283; A61B 17/7266; A61B 17/7225; A61B 17/7233; A61B 17/7258
(Continued)

(56) References Cited

U.S. PATENT DOCUMENTS

| 4,453,539 A | 6/1984 | Raftopoulos et al. |
| 4,492,226 A | 1/1985 | Belykh et al. |

(Continued)

FOREIGN PATENT DOCUMENTS

WO 02058575 A1 8/2002

*Primary Examiner* — Pedro Philogene
*Assistant Examiner* — David C Comstock
(74) *Attorney, Agent, or Firm* — Hayes Soloway PC (57) ABSTRACT

Intramedullary fixation device, having an intramedullary rod (2) which is provided for insertion thereof into a bone (1) and consists of a central screw (4) having a first free end comprising a stopper (7) and a second free end with a pre-tensioning nut (8), an alternating series of expanders (3) and bolts (5) being arranged in between, the bolt surfaces in contact with the expanders (3) having a wedge shape. The bolts (5) or expanders (3) may have no, or one or more variations in the dimensions of the different geometric
(Continued)

parameters, in accordance with the adjacent expanders, along the length of the implant, and the central screw (4) may have a variable cross section. The device may have different additional components, such as an osteotomic base (9) for fixation of the musculature. The device promotes maximum nailing limited between these elements and produces a controlled peripheral radial deformation.

15 Claims, 4 Drawing Sheets (51) Int. Cl.
*A61F 2/30* (2006.01)
*A61F 2/78* (2006.01)
(52) U.S. Cl.
CPC .............. *A61F 2002/30777* (2013.01); *A61F 2002/7887* (2013.01)
(58) Field of Classification Search
USPC .............................................. 606/62, 63, 68
See application file for complete search history.

(56) References Cited

U.S. PATENT DOCUMENTS

| 4,590,930 A * | 5/1986 | Kurth ................ A61B 17/7258 |
| | | 606/63 |
| 8,133,226 B2 * | 3/2012 | Chou ................ A61B 17/7291 |
| | | 606/63 |
| 2007/0060891 A1 | 3/2007 | Skiera et al. |
| 2012/0065638 A1 | 3/2012 | Moore |

\* cited by examiner

Figure 5

INTRAMEDULLARY FIXATION DEVICE

CROSS-REFERENCES TO RELATED APPLICATIONS

This patent application claims priority from PCT Patent Application No. PCT/ES2017/070619 filed Sep. 18, 2017, which claims priority from ES Application No. P201631220 filed Sep. 19, 2016. Each of these patent applications are/which is herein incorporated by reference in its/their entirety.

FIELD OF THE INVENTION

The present invention relates to an uncemented intramedullary fixation device, which is inserted in the medullary canal of long bones and allows arranging elements of internal or external prosthesis or assisting in the reconstruction of fractures, among other uses.

DESCRIPTION OF RELATED ART

There are several ways for fixation of elements by means of press fitted intramedullary rods. The most common is that of inserting a rigid rod being percussed into the bone. In exo-prosthetization applications, the OPRA system performs machining of a thread in the bone wall so as to fix the implant. These implant methods may cause damage or even fractures in the bone wall, thus there is a need of avoiding insertion of the rod in the bone with interference by hammering, or machining threads in the intramedullary canal.

WO 02058575 describes expansion modules (10) formed by six deformable longitudinal portions (12), the ends of which having a blocking mechanism in the manner of a ratchet (28b). This element (28b) is used exclusively for allowing the expansion module (10) to be blocked with respect to the adjacent element or compression coupling (24) in the axial direction. The element 28b is exclusively used for fixing the inner elements of the implant to each other by means of a ratchet mechanism, so that the whole system is connected in the axial direction and the mounting and demounting operation is rendered easy, but this element does not produce radial expansion of any element.

The document being nearest to the invention, U.S. Pat. No. 4,453,539, describes a fixation system by means of three flanges (FIG. 4) or by means of balls (FIG. 7), which are retractably extracted from inside the guiding cylinder by the action of the central conical element. The system disclosed is a mechanism formed by retractable flanges connected to elastic retaining rings, while in the one disclosed in the present invention a single element is used which is radially deformed, the behaviour of both of them being different. The flanges or balls move outwardly by the action of the central conical elements, however, these elements do not have a geometry which restrains the maximum nailing, but said maximum nailing is limited exclusively by the screw distance between the two opposing central conical elements.

The retractable flanges are chamfer-shaped at the inner peripheral edge thereof in order to make interaction with the bolts easier, but they are not introduced through the central screw in any case. The system described in U.S. Pat. No. 4,453,539 does not guarantee that all the chamfer surface of the retractable flanges is in contact with the surface of the central conical element, which means that the piece usually acts as a cam with a significant point contact. The fact of using three flanges or balls produces point stress on the bone in the areas where the flanges or balls contact the bone.

BRIEF SUMMARY OF THE INVENTION

The problem being solved by the invention is to avoid exceptional high stress in certain areas of the bone by improving distribution along the bone, improving stress damping and avoiding possible undesired remodelling or point damage in the bone.

The solution found by the inventors is a rod comprising wedge bolts and expanders through which a central screw is inserted, thus promoting a maximum limited nailing among these elements and producing a controlled radial peripheral deformation.

In the disclosed system exceptional stress is avoided when using at least an expanding element which, upon radial deformation thereof, contacts with its entire outer peripheral surface into the whole inner wall of the bone being adjacent to said surface of the implant. This effect, together with the possibility of adapting some geometric parameters such as the wedge angle of each pair of bolt-expander, allows a more homogeneous distribution of the stress along the entire wall of the intramedullary canal.

The device comprises a rod which improves and facilitates the method of implantation and initial fixation of the prosthesis to the medullary canal, as well as stress and deformation transmission to the bone in order to re-establish the physiological processes of bone apposition and resorption. Furthermore, it also facilitates the method for implant extraction after the osseointegration.

It is a device with interference being distributed along the medullary canal, and with variable rigidity of the rod, which reduces stress damping and improves bone apposition process, unlike the systems with high elasticity modules, which accumulate, in a small area, stress transmission to the bone being derived from the loads to which the system is subjected during normal use thereof.

Unlike most of the current rigid systems which accumulate stress and deformations in the bone at one of the ends of the rod, promoting excessive bone growth in said zone, while bone resorption is produced in the rest of the cortical bone, simulations have shown how the device of the invention is capable of transmitting the physiological levels of stress and deformations to the bone, in an homogeneous and extended manner, along the entire wall of the medullary canal, and is adapted to the state of the loads to which the system is subjected at every moment.

Concretely, the intramedullary fixation device of the invention comprises an intramedullary rod provided for insertion thereof into a bone, the rod being formed by a central screw with a first free end having a stopper and a second free end with a pre-tensioning nut and an alternating series of expanders and bolts arranged in between. The bolt surfaces in contact with the expanders increasingly reduce in both directions the cross section along the longitudinal direction (hereinafter referred to as wedge shape), becoming spindle-shaped, with either a round, square or any other type of section.

Preferably, the rod bolts may have one or more variations in the geometric parameters dimensions, according to the adjacent expanders, along the rod length, and/or the central screw may have a variable section in its length.

This basic solution may be fulfilled in different ways:

Adding a solid cylinder between the stopper and the pre-tensioning nut, among the other bolts and expanders, replacing one or more of the latter. Preferably, the bolt being adjacent to the solid cylinder will be changed by a modified one, so that the wedge faces only contact the adjacent expander.

Adding, to the second free end of the rod, an osteotomic base with an anchoring for an exo-prosthesis which may be provided with a percutaneous collar. The osteotomic base will be able to fix the free ends of part of the residual musculature, by means of a series of grips formed by bars being perpendicular to the rod axis.

Arranging a prosthetic component in the second free end of the rod. For example, a femur head.

Including in the second free end of the rod a cylinder being drilled for passage of fixing nails.

Preferably, between each pair of contiguous expanders there is a space being aligned with the central area of the bolts. That is, the expanders do not touch each other so as to allow bigger clearance or freedom of movement between them, promoting bone deformation. If desired, that space can be filled with a washer made of soft silicone or a similar material with a very low elasticity module.

The transmission of load from the rod to the bone by friction is controlled at each point by means of the ratio between the rod and bone rigidity, and by radial deformation of the expanders caused by nailing. In this system, the first effect is controlled varying the section of the central screw, the expander elements and the bolts. The second one is controlled by means of the tilting or conicity of the expanders and bolts in each area and the length thereof, generating an additive effect of the friction forces existing among the different components. This makes it easier for the bolts being further away from the load to be introduced, to a greater or lesser extent (depending on the geometric variation being used), into the conical hole of the cylinder when subjected to loads, thus generating variable interference levels along the length of the intramedullary canal, also obtaining a variable rigidity rod.

In the case of exo-prosthesis fixation, the osteotomic base offers a series of longitudinal grips designed so as to accommodate the functional suture from the residual musculature. This type of functional suture is provided for creating an attachment being enough resistant and stable so as to be able to develop a pre- and post-amputation muscle rehabilitation programme, intended to reactivate functionality of certain muscle groups avoiding the atrophy process of these tissues, thus improving the proprioception function and transmitting the bone the stress levels generated by the sutured residual muscle groups.

BRIEF DESCRIPTION OF THE SEVERAL VIEWS OF THE DRAWINGS

For a better understanding of the invention, the following figures are included.

FIG. 2: A) view of an exemplary osteotomic base applicable to the device. B) Section of an example of a device having an osteotomic base. C) Examples of the positioning of the osteotomic base in the body of a patient.

DETAILED DESCRIPTION OF THE INVENTION

The following is a brief description of an embodiment of the invention as an illustrative and non-limiting example thereof.

The invention refers to a device for fixation thereof to the intramedullary wall of a bone (1), consisting of a rod (2) and usually an additional component that will depend on the objective intended.

The rod (2) is formed by a number of expanders (3) (which can be decoupled from the central bar), made by biocompatible, polymer or metal modules or cylinders. For example, the expanders (3) will be coated with a titanium alloy, hydroxyapatite or any other biocompatible coating material which promotes subsequent osseointegration with the bone (1). The modules will be arranged in a central screw (4) passing through the expanders (3) via an inner hole.

Between each pair of consecutive expanders (3) corresponding bolts (5) are arranged, being also mounted in the central screw (4) (although they can be decoupled therefrom), the faces of which being in contact with the expanders (3) are wedge shaped, so the central part of each bolt (5) has a bigger section than that of both ends. The bolts (5) will have the complementary geometry, but a lower section so that interference is produced between them. The length of the conical areas, as well as that of the spaces between the expanders (3), can also be variable.

By arranging a wedge in both directions of the bolt (5), any tensile or compression stress onto the rod (2) increases nailing or wedging thereof. Thus, the device is capable of generating additional stress onto the bone, both in the lower limb, which mainly features compression work, and in the upper limb, which mainly features tensile work.

Thus, upon getting two consecutive expanders (3) nearer, the wedge geometry of the elements will produce progressive nailing of said components to each other, causing expansion of the expanders (3) in a radial direction and an increase in the diameter thereof. Nailing can be limited by geometric stoppers (3a, 5a), both in the expander and in the bolt, upon contact of either the flat end being perpendicular to the axial axis of the bolt (5) wedge, or the central step described below, with the corresponding surface of the expander (3). Thereby, the length of the bolts and the position of the central step allow controlling the level of nailing between a bolt and the corresponding expander. Thus, upon contact of the expander (3) and the bolt (1), pressure is exerted onto the latter producing the initial friction anchoring of the device to the bone (1), thus guaranteeing that the breaking stress of the bone is not exceeded.

In order to facilitate this expansion, the expanders (3) may be provided with lines of weakness (6), slots or any other solution which reduces the rigidity thereof. These slots are also used for obtaining a greater fixation of the implant to the bone and avoiding the relative rotation between both components.

The central screw (4) will have a first stopper (7) at a first free end that will be the one to be first introduced in the medullary canal of the bone (1), which can be integral to the central screw (4), or be a separate element either threaded or fixed by means of a pin. At the second free end of the central screw (4) a pre-tensioning nut (8) will be arranged which can be threaded onto the second free end so as to produce expansion of the expanders (3). It is also possible that the pre-tensioning nut (8) is integral to the central screw (4), and rotation thereof causes it to be threaded in the stopper (7). In some applications, the pre-tensioning nut (8) will be cylindrical so that it can rotate inside the medullary canal and perform the pre-tensioning, while in others it may have hexagonal or any other shape. Preferably, it will be provided with a step at the part thereof inwardly oriented so as to give the bone support and compression.

The stopper (7) may also have a wedge similar to that of the bolts (5), or comprise an anchoring system formed by a nailing element, such as that being described below.

Generally, the central screw (4) goes through the additional component of the device, so that the pre-tensioning nut (8) also performs attachment between the additional component and the rod (2). If desired, a conical surface may be provided for the nearest expander (3). The same may apply for the stopper (7). Preferably, the additional component will have means to avoid rotation of a piece ad-hoc in the additional component, with the contact surface not being cylindrical so that there is no possible axis of rotation.

Figure 5:
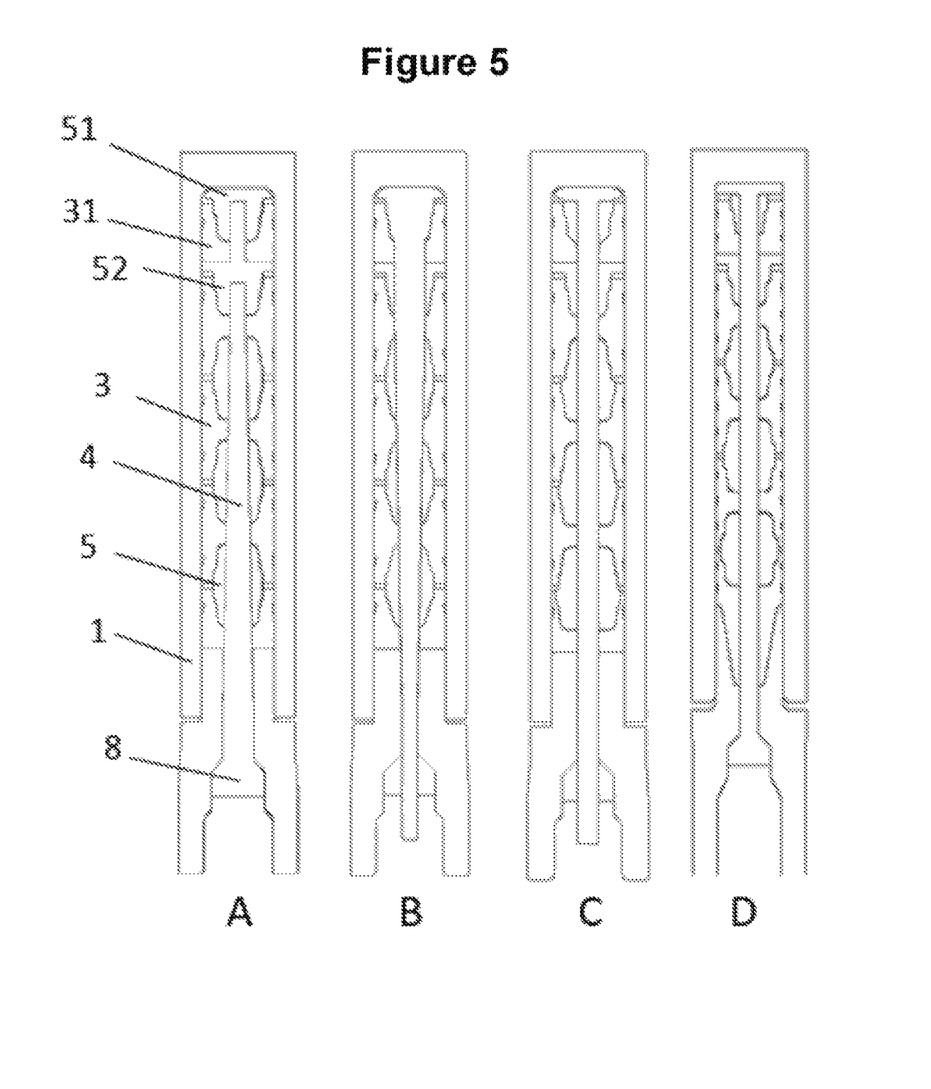
FIG. 5: examples of the positioning of bolts, screws or central cables and expanders, having variable section in customized applications.

The system designed allows realizing a customization of the implant according to the specific needs of the patient's anatomy, the type of application (endo- and exo-prosthesis of an upper or lower limb) and the level and type of surgery to be done. This is achieved thanks to the combination of several geometric variations of the components with the purpose of controlling the progressive nailing (FIG. 5):

The size and slope of the bolts (5) and their arrangement may vary (from bigger to smaller or vice versa), and the expanders (3) may vary their inner shape so as to fit the bolt (5).

The central screw (4) section along the longitudinal direction may also vary.

Control of the nailing or wedging degree by means of changes of the geometry in the wedge (length of the bolts and geometric stoppers (3a, 5a)).

Some examples of application of these variable geometries are as follows: in order to obtain a uniform distribution of stress in the bone, the most convenient option is that the central screw (4) rigidity and the nailing angle of the bolts (5) and expanders (3) increase as we move away from the free end of the rod. In order to fix an external prosthesis in the upper limb, it is convenient to increase interference between the bolts (5) and the expanders (3) so as to keep the same levels of nailing on the bone. Since the maximum nailing is limited by the components geometry, in order to achieve a greater maximum nailing, interference may increase between both elements by increasing the bolt (5) section, keeping the expander (3) section with the original dimensions, or reducing the expander (3) section keeping that of the bolt (5) with the original dimensions. This set of sections allows selecting and optimizing the areas of implant fixation and the transmission of stress and deformations to the bone.

However, in a lower limb, the rod will mainly support compression loads and the external load will add by itself to the pre-tensioning.

FIG. 5 shows several ways of realizing this variation:

A. Central screw having a variable cross section and expanders and bolts with a constant nailing angle.

B. Central screw having a variable cross section in a direction being opposite to the previous one and variable nailing angles.

C. Central screw having a constant section and expanders and bolts with a variable cross section.

D. Similar to FIG. 5C, but with symmetrical bolts.

Each one of the above combinations introduces changes in the transmission and distribution of stress and deformations in the bone. The different levels and patterns of stress and deformations being generated over the bone using either combination may be used for optimizing the function of the implant based on the application, dimensions of the bone section, load levels to be supported etc.

The combination shown in FIG. 5A produces a different stress and deformation level and pattern, depending on the step at which it is. During the implantation and osseointegration with no load, there is a stress pattern observed which divides the bone (1) in two areas, the area of the upper half with higher stress, and the area of the lower half with lower stress. However, once the implant is completely osseointegrated and the bone (1) has adapted to the initial deformation, when the system is subjected to loads, there appear areas in the bone (1) matching the spaces between the expanders (3), with stress above the physiological ones, and the rest of the medullary canal is shown with stress at the level of the physiological ones. This type of combination could be used, for example, in cases where a higher force is required for fixing the implant to the bone (1), both at the osseointegration phase with no load, and in the long term period. It could also be used in patients with higher thickness of the bone (1) wall, who need a bigger stimulus for bone apposition, or it can be used the characteristic pattern of initial stress and deformations dividing the bone (1) into two stress areas so as to stabilize fractures located in a concrete half of the bone, without exerting excessive force in said area, while achieving a higher fixation force of the nail in the other half of the bone (1).

However, the combination shown in FIG. 5B, during the implantation and osseointegration phase with no loads, it is capable of generating homogeneous stress distribution along the whole wall of the bone canal. The levels of stress generated at this phase are at the level of the lowest stress generated by the previous combination for the same phase. This can be used in applications where the structural quality of the bone (1) is bad or is weakened along its entire length, or in smaller bone (1) sections. During the osseointegration phase with the combination of FIG. 5B there appears a stress pattern showing a division of the bone (1) in two areas (the same effect being produced with the previous combination for the initial phases). The half of the bone (1) being nearest to the prosthetic component or ostotomic base is under higher load levels than the upper area (always within the physiological load levels). This effect can be used depending on the limb to be prosthesized (upper or lower) and the type of load to support (tensile or compression stress) so as to homogenize the total stress (due to the bending moments and those due to the expansion of elements) which are transmitted along the bone (1).

Using other geometric combinations (not shown in the Figures), as for example that shown in FIG. 5A adding the variation of angles of the conical elements, a pattern of stress is obtained being more similar and homogeneous in all phases (initial implantation, no-load and long term osseointegration).

FIGS. 5C and 5D show two ways of varying the cross section of the bolts (5) and the expanders (3) along the implant length. In both figures the wedge section of the bolts (5) is reduced in the direction towards the first end of the central screw (4), while the expanders (3) section is widened. The difference between both embodiments lies in the element where the section variation is introduced. In an image, the change of section is done inside at least one bolt (5), the expanders (3) keeping symmetry with respect to the transverse plane. In the other section it varies inside one or more expanders (3), the bolts (5) being symmetrical. The effect this geometric variation introduces in the levels and distribution of stress and deformations is the same in both images, however, it is preferred to realize the changes of section inside the expanders (3), rather than in the bolts (5), so as to avoid stress concentrations which appear in the step changes in the bolts (5). This geometric combination produces a pattern of stress being different to those previously set forth, thus promoting a progressive stress increase as it moves away from the load application area, regardless if it is in the reducing or increasing direction of the components section.

If the central screw (4) reduces its section as it gets nearer the first free end (FIG. 5C), it is not possible to introduce the central screw (4) prior to the insertion of the bolts (5) and expanders (3). In this case, in order to prevent the elements from being misaligned and to introduce the central screw (4), the stopper (7), uncoupled from the central screw (4), comprises a fixation system consisting of a first half bolt (51), combined with an expander (31) means, and a second half bolt (52). The second half bolt (52) has, at its wedge-less end, a threaded pin which is introduced and threaded in the first half bolt (51), while in the wedged side it has a threaded hole for the central screw (4). Thus, the stopper (7) is nailed in the suitable position prior to the introduction of the other elements of the device, by threading the half bolts (51, 52) tightening the expander (31) means. This stopper (7) can also be applied to any other form of central screw (4), being possible to replace the threaded pin by the central screw (4) itself when this is installed from the beginning.

When the bolts (5) have different geometric characteristics, the expansion of each expander (3) or pair of expanders (3) is different, so the fixation varies along the bone. Similarly, bolts (5) can be arranged having wedge ends of different size or maximum section, which involves a central step (such as that of the upper bolt (5) of FIG. 5C), so that the change is more sudden.

By combining the intramedullary rod (2) with the different components of implants, it is intended to encompass different applications, as it will be indicated in the examples described below.

Figure 2:
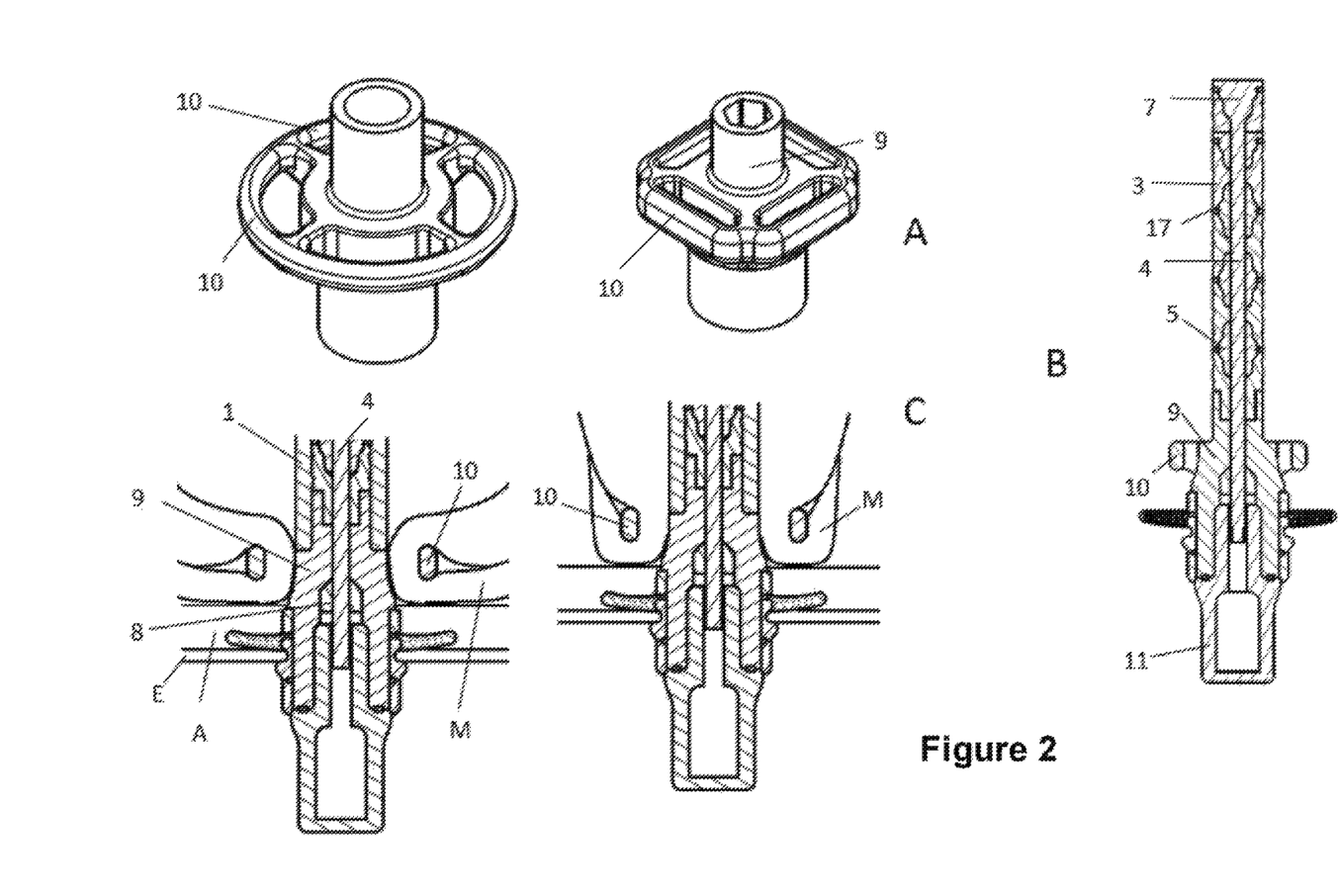

FIGS. 2A and 2B show an example for exo-prosthetization of limbs by means of DSA (direct skeletal attachment) technique. FIG. 2C shows how to couple it to the bone (1), and two ways of coupling it to the musculature (M), to the adipose tissue (A) and to the epidermis (E).

This case requires an osteotomic base (9), which can be provided with grips (10) intended for functional suture of the musculature (M) by means of pseudotendons surrounding these grips (10).

As it can be appreciated in the figures, each grip (10) comprises a curve or straight bar, without edges, being perpendicular to the rod (2). The number of grips (10) will depend on the quantity of muscles to be fixed, but it will be a minimum of 2.

Usually, the end of the osteotomic base (9) opposite the rod (1) will pass through the soft tissues and will be preferably threaded so as to provide a percutaneous collar as those shown in the application US2007060891 (incorporated herein by reference). The collar will remain underneath the epidermis (E) which is passed through by the end of the osteotomic base where said collar is fixed, and which is also used as the exo-prosthesis anchoring element (11). It is also possible not to provide grips (10) but a series of orifices for yarn to pass through for the musculature suture to the osteotomic base (9), as it is already known in the art.

The osteotomic base (9) will connect with the last expander or bolt through the second free end of the rod (2), by means of a tongue and groove connection for example, so that the compression loads the prosthesis undergoes during daily activities are transmitted to the rod (2) and assist in the nailing.

Any tensile load will be transmitted from the osteotomic base (9) to the bone by means of two ways:

By contacting the osteotomic base and the pre-tensioning thread fixed to the central screw (4), and through this screw to the bolts and the expander elements exerting a pressure against the bone.

Through direct attachment between the intramedullary cylinder of the osteotomic base and the bone area in contact with said cylinder. The bending stress will pass directly from the osteotomic base (9) to the bone (1) through direct contact thereof, for example through a cylindrical end of the osteotomic base (9) partially introduced in the medullary canal. Moreover, by means of the suture of the main musculature of each limb to the grips (10), the muscles partly compensate the stress of the bone (1) due to bending loads, which in turn allows them to keep the musculature active and to avoid flaps of distal tissues.

Figure 3:
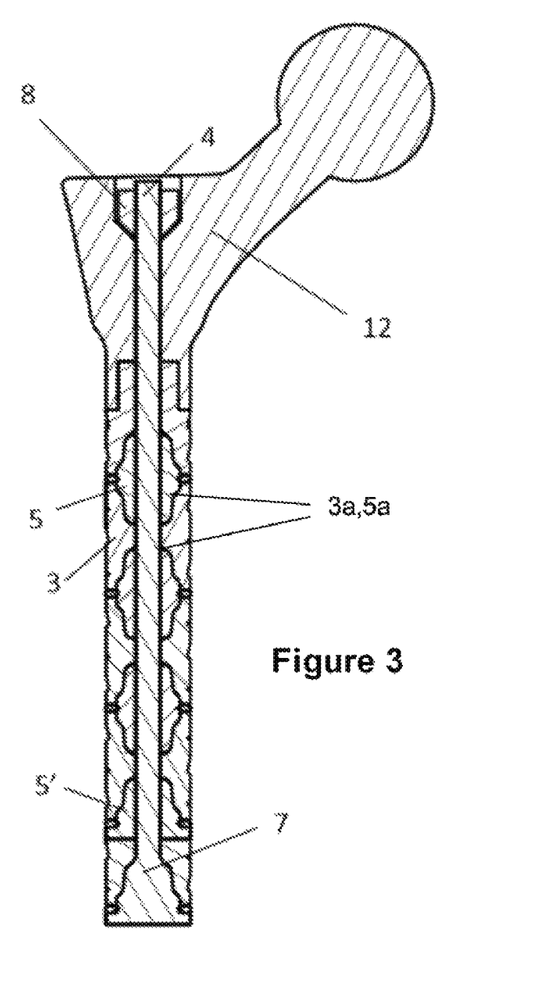
FIG. 3: section of a third embodiment, with an example of a prosthetic component.

FIG. 3 shows the application in endo-prosthetization of large bones joints. In this case the additional component is a prosthetic component (12) for auricular replacement of the femoral head.

This has a longitudinal through hole for receiving the central screw (4) and the pre-tensioning nut (8).

Figure 4:
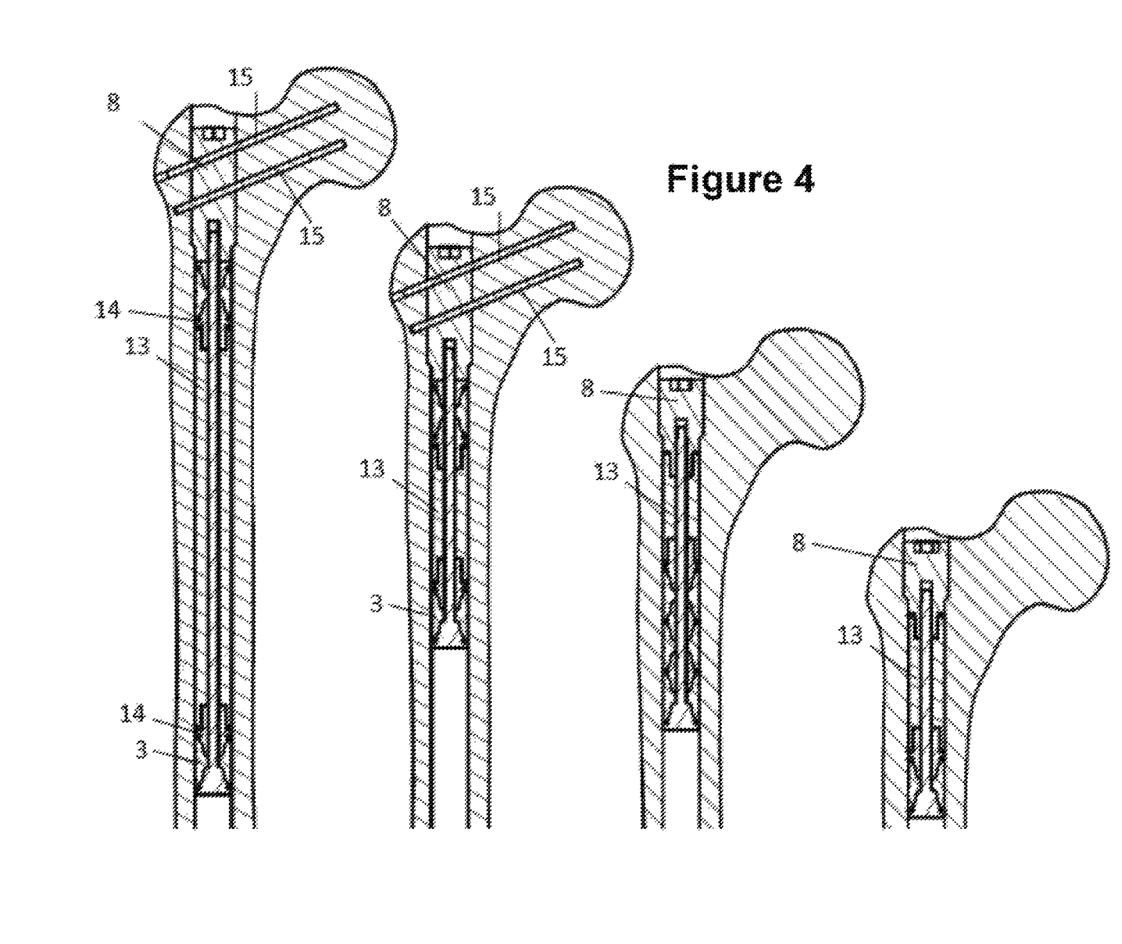
FIG. 4: several examples of the device applied to fractures.

FIG. 4 shows several examples of application in fracture reconstruction. The system is capable of compressing and stabilizing the different parts of the bone (1) being fractured after the damage suffered in a simple, safe, direct way and without the need of machining and aligning through holes in the diaphyseal bone which weaken the structural section of the bone wall, involve high technical difficulty and an increase in the surgery time.

In the case of fractures, it is suggested to include inside the rod (2), combined with the expanders (3) and bolts (5), a polymer or metal solid cylinder (13). As it can be seen in FIG. 4, the objective of the solid cylinder (13) is to stabilize the area of the fracture corresponding to the positioning place thereof in the rod (2). Thus, there is expansion in the damaged area. As it is not expandable, the bolt (5) insertion in the ends of the solid cylinder (13) will not affect the dimensions thereof. In any case, it is preferred to arrange a specifically adapted bolt (14), with a wedge end for expansion of the expander (3) and the other with the relevant hook for the solid cylinder (13). According to the position and length of the solid cylinder (13) the adapted bolt (14) will be arranged at one end or at both.

If it is necessary the passage of nails (15) for fixation of the head of the bone (1), the pre-tensioning element or nut (8) will be a drilled cylinder which allows the positioning of these nails in the intended orientation.

For fractures just below the greater trochanter or which are too near the second free end of the central screw (4) (epiphysial area), it is proposed to dispense with the system of expander (3) and bolt (5) in the second free end, and to generate the bone (1) stabilization (system pre-tensioning) by means of a pre-tensioning nut (8) (FIG. 4). In this case, the attachment between the cylindrical pre-tensioning nut (8) (which can be drilled for fixation nails to pass through) and the solid cylinder (13) must allow relative rotation thereof by means of a cylindrical tongue and groove attachment. In this type of fractures, in case of needing higher stability along the canal, expanders (3) can be added at the first free end of the screw so as to achieve higher tensile force and a better transmission and distribution of the stress and deformations along the medullary canal.

In general, the rod (2) of the device can be adapted to different prosthetic ends by machining a longitudinal hole therein which allows pre-tensioning and fixation of said end to the rod (2) through the central screw (4) and the pre-tensioning nut (8).

Figure 1:
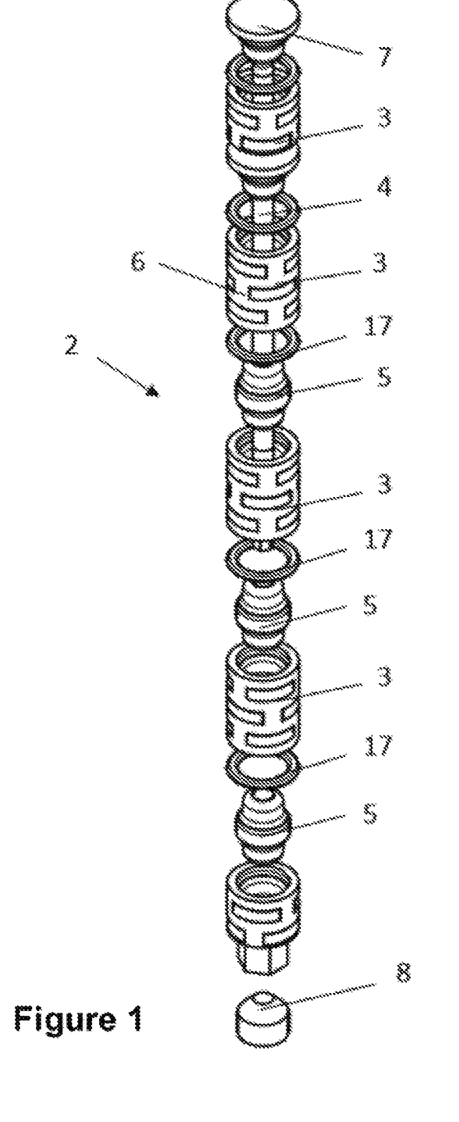
FIG. 1: an exploded view of a first exemplary embodiment of the device.

As FIG. 1 shows, preferably a space will be left between each pair of expanders (3), aligned with the bolts (5) at the central area thereof. Where appropriate, a soft silicone washer (17) that can be part of the bolt (5) or the expander (3). These spaces (with an inconsiderable elasticity module) influence in the way in which stress and deformations are transmitted to the bone when the system is completely osseointegrated and subjected to loads, thus allowing the bone (1) to compress or stretch along its length.

Normally, the process of implantation and initial fixation of the rod to the medullary canal, once it is evacuated, inside the bone (1), is initiated by introducing the central screw (4) through the first free end where the stopper (7) is arranged. Subsequently, the bolts (5) and expanders (3) are progressively introduced without interference with the bone in the initial insertion. If it is necessary because of the application, a solid cylinder (13) is introduced in the desired position.

The additional required component is added, and the pre-tensioning nut (8) is introduced. Upon tightening thereof, it takes place progressive deformation of the expanders (3), which produce progressive nailing of the intramedullary components to the bone. Thus, it is avoided to use implantation methods consisting of machining a thread in the medullary canal or pressure tapping the rod, which seriously damage the endosteum and may generate the bone fracture during implantation.

In case the bolts (5) and the expanders (3) are coupled to the central screw (4), for example by means of a thread, they must be independently inserted and threaded, generating wedging and fixation of each element separately when being introduced into the canal and fixed to the screw.

The expanders (3) and bolts (5) are provided with at least one surface (3a, 5a), changing its inclination with respect to the wedge angle, and which upon contacting each other limit the nailing thereof. That is, the geometric stopper limits the maximum interference between the expander and the bolt, thus controlling the maximum radial deformation of the expander and the maximum stress transmitted to the bone (1).

Some geometric combinations of the intramedullary rod being developed generate additional stress and deformations onto the bone during the osseointegration phase, and once the system is completely osseointegrated, depending on the acting physiological loads, by means of the progressive interference generated upon interaction between the several components (active system). Due to wedge nailing in both directions of the load, all the combinations of the rod (2) are capable of producing interference with the medullary canal and the consequent fixation thereto during tensile and compression loads, even without the need of osseointegration being produced.

Anchoring is effective even when the bone is adapted to the initial pressure and the mounting pre-tensioning the rod exerts on the canal walls disappears, but it is not osseointegrated yet. Under these conditions it is possible to initiate early rehabilitation that improves the osseointegration process.

Regarding the extraction method, the designed device allows extraction of the rod (2) from the medullary canal without damaging the structural integrity of the bone (1), as it allows avoiding the attachment between the cylinders and the bone in a simple and direct way. The pre-tensioning nut is removed and the stress from the different elements is released. Once being completely destressed, the central screw (4) can be removed. Since, preferably, the expanders will be of a polymeric material, attaching thereof to the bone may be eliminated by using a crown drill having a diameter that matches that of the medullary canal.

The invention claimed is:

1. An intramedullary fixation device provided for being inserted into a bone, having:
    a plurality of expanders, having a surface with a central area and two ends comprising conical or pyramidal inner holes, defining a wedge angle and having the smaller section oriented towards the central area,
    a plurality of bolts, having a surface with two ends and a central part having a bigger transversal section than both ends, thus, the surface having a spindle shape, a geometry complementary to the expanders and a slightly greater section, wherein the ends are intended to be introduced in the inner holes of the expanders, so that, interference between the bolts and the expanders and radial expansion of the expanders are produced,
    an intramedullary rod comprising a central screw, with a first free end having a stopper and a second free end having a pre-tensioning nut, for being introduced through an inner hole of an alternating series of the plurality of expanders and the plurality of bolts,
    wherein the surfaces of the expanders and bolts changes its inclination with respect to the wedge angle, so that, the nailing is limited upon contacting each other, and wherein the stopper limits the maximum interference between the expanders and the bolts, thus, controlling the maximum radial deformation of the expanders and the maximum stress transmitted to the bone.

2. The device according to claim 1, wherein the conical or pyramidal holes of the bolts have different wedge angles, lengths, sections and maximum interferences, in accordance with the adjacent expander holes, along the rod length.

3. The device according to claim 1, wherein the rod further comprises a solid cylinder between the stopper and the pre-tensioning nut, for being connected to the expander by a bolt having a geometry complementary to said solid cylinder.

4. The device according to claim 3, wherein the pre-tensioning nut is cylindrical and arranged adjacent to the solid cylinder at the second free end of the rod, being provided with a step in the area oriented inwardly, and wherein the attachment between the pre-tensioning nut and the solid cylinder allows relative rotation between both.

5. The device according to claim 4, wherein the pre-tensioning nut is drilled for fixation nails to pass through at the second free end of the rod.

6. The device according to claim 1, further comprising, at the second free end, an osteotomic base with an anchoring element for an exo-prosthesis and a percutaneous collar.

7. The device according to claim 6, wherein the osteotomic base has a series of grips, consisting of bars placed perpendicular to the rod.

8. The device according to claim 6, wherein the osteotomic base has a cylindrical end for partial insertion into the bone.

9. The device according to claim 6, wherein the osteotomic base has a cylindrical threaded end designed for passing through soft tissues and adapted to connect a percutaneous collar and an exo-prosthesis.

10. The device according to claim 1 further comprising a prosthetic component at the second free end of the rod.

11. The device according to claim 1, further comprising a space or area between each pair of expanders having a negligible elastic module, and being aligned with the central part of the bolts.

12. The device according to claim 11, further comprising a washer made of soft silicone or a similar material in the space between expanders.

13. The device according to claim 1, wherein the central screw has a variable section in the longitudinal direction.

14. The device according to claim 1, wherein the stopper is decoupled from the central screw and consists of a first half bolt, having a wedge onto which half expander is arranged, and a second half bolt, having a pin threaded into first half bolt and a threaded hole of the central screw.

15. The device according to claim 1, wherein the expanders have lines of weakness.

\* \* \* \* \*